(12) United States Patent
Chen

(10) Patent No.: US 7,878,065 B2
(45) Date of Patent: Feb. 1, 2011

(54) ULTRASONIC INSPECTION APPARATUS

(75) Inventor: Wei Chen, Shenzhen (CN)

(73) Assignees: Hong Fu Jin Precision Industry (ShenZhen) Co., Ltd., Shenzhen, Guangdong Province (CN); Hon Hai Precision Industry Co., Ltd., Tu-Cheng, Taipei Hsien (TW)

( * ) Notice: Subject to any disclaimer, the term of this patent is extended or adjusted under 35 U.S.C. 154(b) by 388 days.

(21) Appl. No.: 12/133,390

(22) Filed: Jun. 5, 2008

(65) Prior Publication Data

US 2009/0107242 A1   Apr. 30, 2009

(30) Foreign Application Priority Data

Oct. 31, 2007   (CN) .................. 2007 1 0202341.7

(51) Int. Cl.
*G01N 29/00* (2006.01)
(52) U.S. Cl. .................. 73/627; 73/606; 73/618
(58) Field of Classification Search .......... 73/627, 73/606, 618, 620, 629, 599, 600, 602
See application file for complete search history.

(56) References Cited

U.S. PATENT DOCUMENTS

| | | | | |
|---|---|---|---|---|
| 4,821,573 A | * | 4/1989 | Nagata et al. | 73/597 |
| 5,302,856 A | * | 4/1994 | Narita et al. | 257/788 |
| 5,359,895 A | * | 11/1994 | Isenberg et al. | 73/582 |
| 5,372,042 A | * | 12/1994 | Jarman et al. | 73/588 |
| 5,600,068 A | * | 2/1997 | Kessler et al. | 73/620 |
| 5,641,906 A | * | 6/1997 | Moore | 73/614 |
| 6,089,095 A | | 7/2000 | Yang et al. | |
| 6,938,488 B2 | * | 9/2005 | Diaz et al. | 73/597 |
| 7,107,852 B2 | * | 9/2006 | Hutchins et al. | 73/598 |

FOREIGN PATENT DOCUMENTS

JP   58011384   *   1/1983

* cited by examiner

*Primary Examiner*—Jacques M Saint Surin
(74) *Attorney, Agent, or Firm*—Frank R. Niranjan

(57) ABSTRACT

An ultrasonic inspection apparatus includes a container containing de-ionized water, at least one limiting member, a loading member, and a cover member. The at least one limiting member, the loading member, and the cover member are disposed in the de-ionized water and between the transmitting transducer and the receiving transducer. The limiting member is supported on the limiting member for loading the integrated circuits to be inspected. The cover member is detachably disposed on the loading member for holding the integrated circuits by a gravitational force of the cover member acting on the loading member.

14 Claims, 4 Drawing Sheets

ULTRASONIC INSPECTION APPARATUS

BACKGROUND

1. Field of the Inventions

The present invention generally relates to ultrasonic inspection apparatuses, and particularly to an ultrasonic inspection apparatus for inspecting integrated circuits.

2. Description of Related Art

Integrated circuits (IC) are widely used in electronic devices. The ICs are fabricated and then packaged. However, pre-packaging, the ICs are inspected for defects including crack and de-lamination etc., caused by environmental conditions. In order to detect these defects, ultrasonic inspection apparatuses are used.

Generally, an ultrasonic inspection apparatus includes a transmitting transducer and a receiving transducer. An IC to be inspected for defects is placed apart between the transmitting transducer and the receiving transducer. During inspection, the transmitting transducer emits ultrasonic waves to the IC. The ultrasonic waves pass through the IC and is received by the receiving transducer on the other side of the IC. Certain defects (such as cracks or de-lamination) can cause certain changes (amplitude and/or phase) in the electrical signals. As such, if the electrical signals are measured when the IC is subjected to ultrasonic waves, certain defects of the IC can be identified. However, when the IC is not stably held in the ultrasonic inspection apparatus, noise may be induced due to vibrations or jitters. Such noise would affect the detection precision of the defects. That is, the ultrasonic inspection apparatus may not accurately measure the degree of defects of the IC.

Therefore, in order to accurately detect the defects, the IC should be stable and free from vibrations or jitters. Thus, providing an ultrasonic inspection apparatus satisfying this requirement is desired.

SUMMARY

An ultrasonic inspection apparatus for detecting defects in integrated circuits is provided. The ultrasonic inspection apparatus operates by projecting ultrasonic waves from a transmitting transducer and receiving ultrasonic waves by a receiving transducer. The ultrasonic waves being passed through or reflected from the integrated circuits. The ultrasonic inspection apparatus includes a container containing de-ionized water acting as a transmission medium of ultrasonic waves, at least one limiting member, a loading member, and a cover member. The at least one limiting member, the loading member, and the cover member are disposed in the de-ionized water and located between the transmitting transducer and the receiving transducer. The limiting member is supported on the limiting member for loading the integrated circuits to be detected. The cover member is detachably disposed on the loading member for holding the integrated circuits a gravitational force of the cover member acting on the loading member.

Other advantages and novel features will become more apparent from the following detailed description of exemplary embodiment when taken in conjunction with the accompanying drawings.

DETAILED DESCRIPTION

Figure 1:
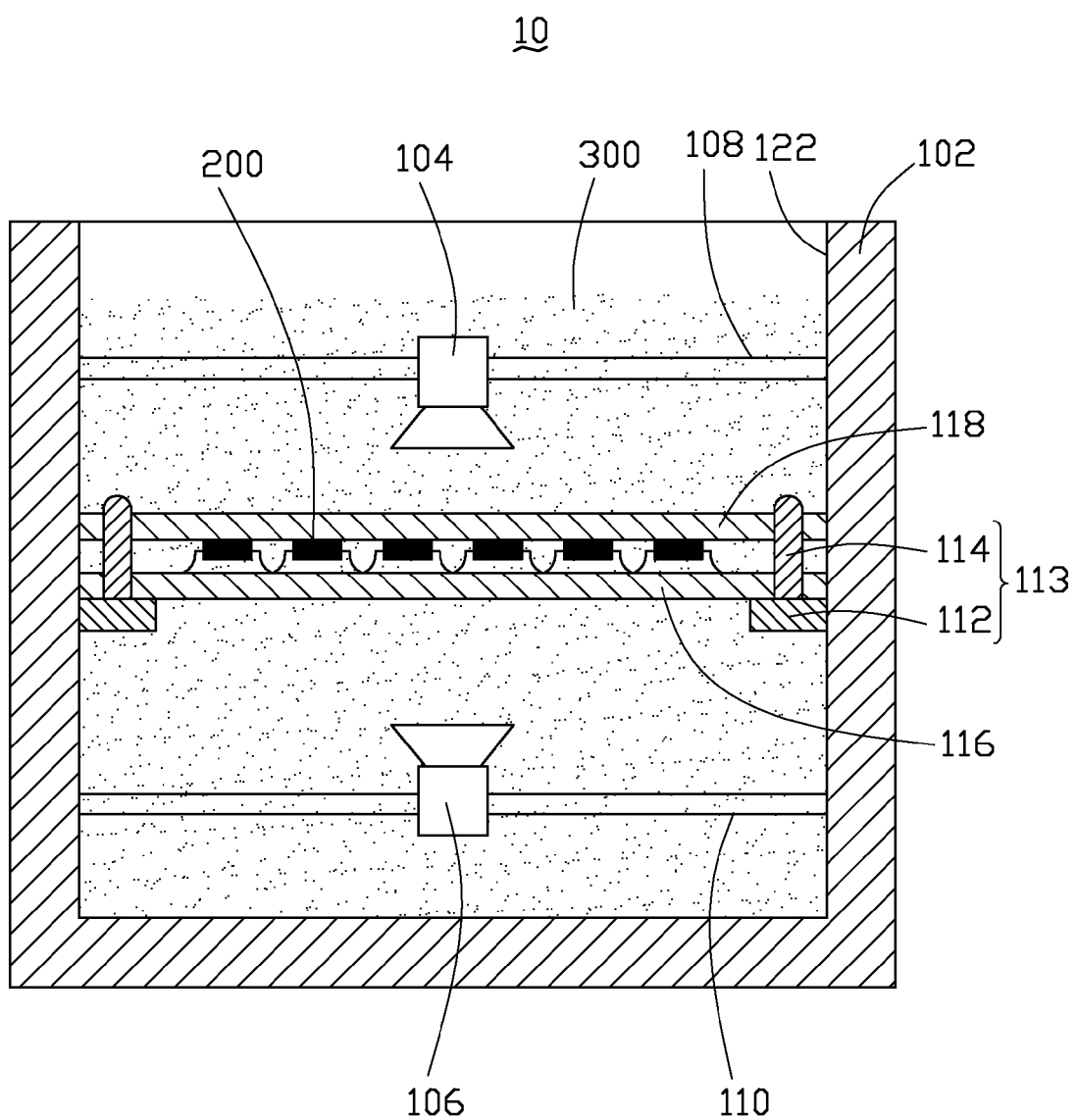
FIG. 1 is a sectional view of a first ultrasonic inspection system in accordance with an exemplary embodiment.

Referring to FIG. 1, a first ultrasonic inspection apparatus 10 in accordance with an exemplary embodiment is illustrated. The first ultrasonic inspection apparatus 10 is provided for detecting defects such as cracks and de-lamination in integrated circuits (IC) 200. The first ultrasonic inspection apparatus 10 includes a container 102, a transmitting transducer 104, a receiving transducer 106, a first positioning member 108, a second positioning member 110, two limiting members 113, a loading member 116, and a cover member 118.

The container 102 defines a cavity 103 for accommodating de-ionized water 300 therein. The de-ionized water 300 acts as a transmission medium for ultrasonic waves.

The transmitting transducer 104 is configured for projecting ultrasonic waves at predetermined frequencies. The receiving transducer 106 is configured for receiving ultrasonic waves that passed through the ICs 200. The receiving transducer 106 is also configured for transforming received ultrasonic waves to electrical signals, and sending the electrical signals to computers (not shown) for detecting the defects. The transmitting transducer 104 and the receiving transducer 106 are attached to the first positioning member 108 and the second positioning member 110 respectively.

The first positioning member 108 and the second positioning member 110 are disposed parallel to each other, and are coupled to internal side walls 122 of the container 102. The first positioning member 108 is configured for moving the transmitting transducer 104 along a first plane indicated by O-XY coordinate plane (see FIG. 2) over the ICs 200, such that the ICs 200 can be scanned. The second positioning member 110 is configured for moving the receiving transducer 106 in synchronization with the transmitting transducer 104 along a second plane parallel to the first plane indicated by O-XY, for receiving corresponding ultrasonic waves from the transmitting transducer 104.

The two limiting members 113 are mounted on two internal side walls 122 on opposite sides of the container 102, and are located between the first positioning member 108 and the second positioning member 110. Each limiting member 113 includes a rib plate 112, and further, a post 114 vertically protruding from the rib plate 112. The rib plate 112 is configured for supporting the loading member 116. The post 114 is capable of being received in corresponding through holes 162, 182 (see FIG. 3) defined in the loading member 116 and the cover member 118.

Figure 2:
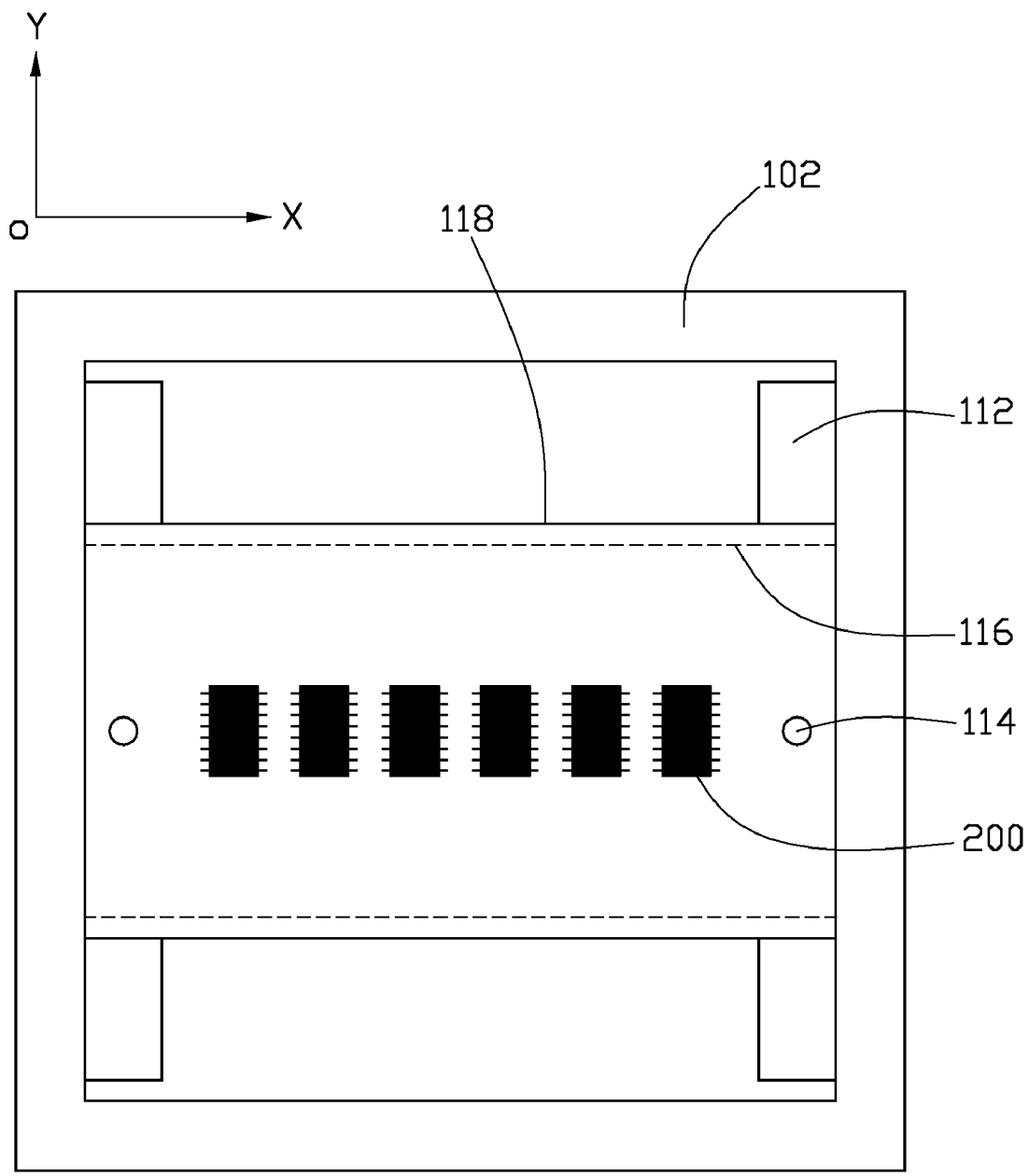
FIG. 2 is a top view of the ultrasonic inspection system shown in FIG. 1.
Figure 3:
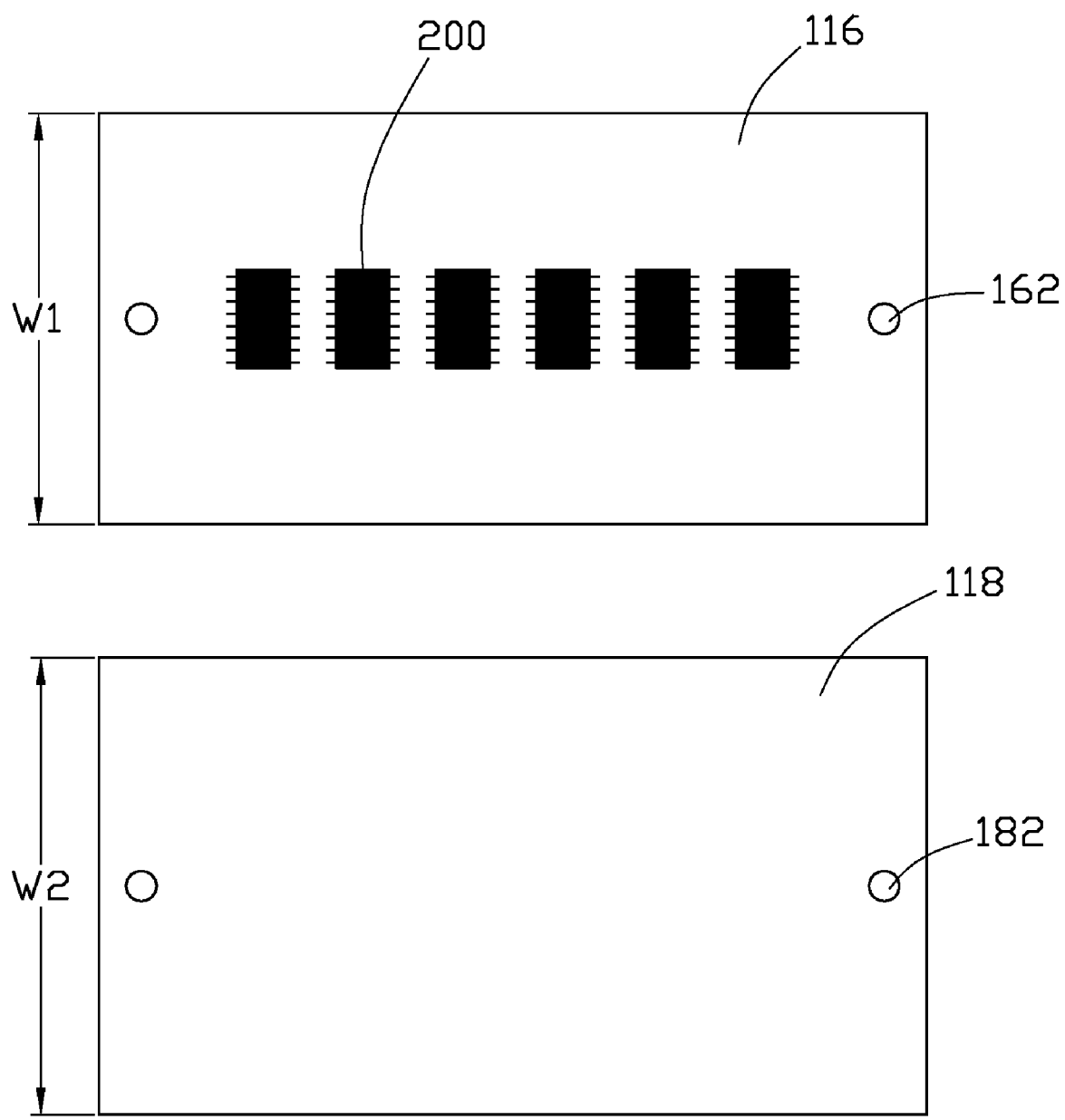
FIG. 3 is an exploded top view of the ultrasonic inspection system shown in FIG. 1.

Referring to FIGS. 2-3, the loading member 116 and the cover member 118 are substantially rectangular plates, and respectively define the through holes 162, 182 therein. The loading member 116 is configured for loading the ICs 200 thereon. The cover member 118 is configured to have a width W1 slightly larger than a width W2 of the loading member 116. As a result, the cover member 118 can easily be separated from the loading member 116, thus, the loading member 116 and the cover member 118 are easily taken out from the container 102. The cover member 118 is configured for covering the loading member 116, and fastening the ICs 200 between the cover member 118 and the loading member 116. Because a gravitational force (a weight) of the cover member 118 acts on the loading member 116, the ICs 200 are firmly held between the cover member 118 and the loading member 116 for detecting defects. The cover member 118 may be made of glass, resin, and other materials.

During inspection of the ICs 200, after the ICs 200 are fastened between the cover member 118 and the loading member 116, the transmitting transducer 104 projects ultrasonic waves to the ICs 200. The ultrasonic waves travel through the ICs 200 from one side to another side. The receiving transducer 106 receives exiting ultrasonic waves from the ICs 200.

The receiving transducer 106 transforms the received ultrasonic waves to electrical signals, and sends the electrical signals to a computer (not illustrated) to detect the defects according to the amplitude or phase information of the electrical signals. Because certain defects (such as cracks or delamination) are known to cause certain changes (such as amplitude and/or phase) in the electrical signals. Thus, if the electrical signals are measured when the IC is subjected to ultrasonic waves, certain defects of the IC can be identified.

The transmitting transducer 104 and the receiving transducer 106 are controlled by the positioning members 108 and 110 to move in synchronization along the O-XY coordinate plane, such that all portion of the ICs 200 can be scanned for detecting defects.

Figure 4:
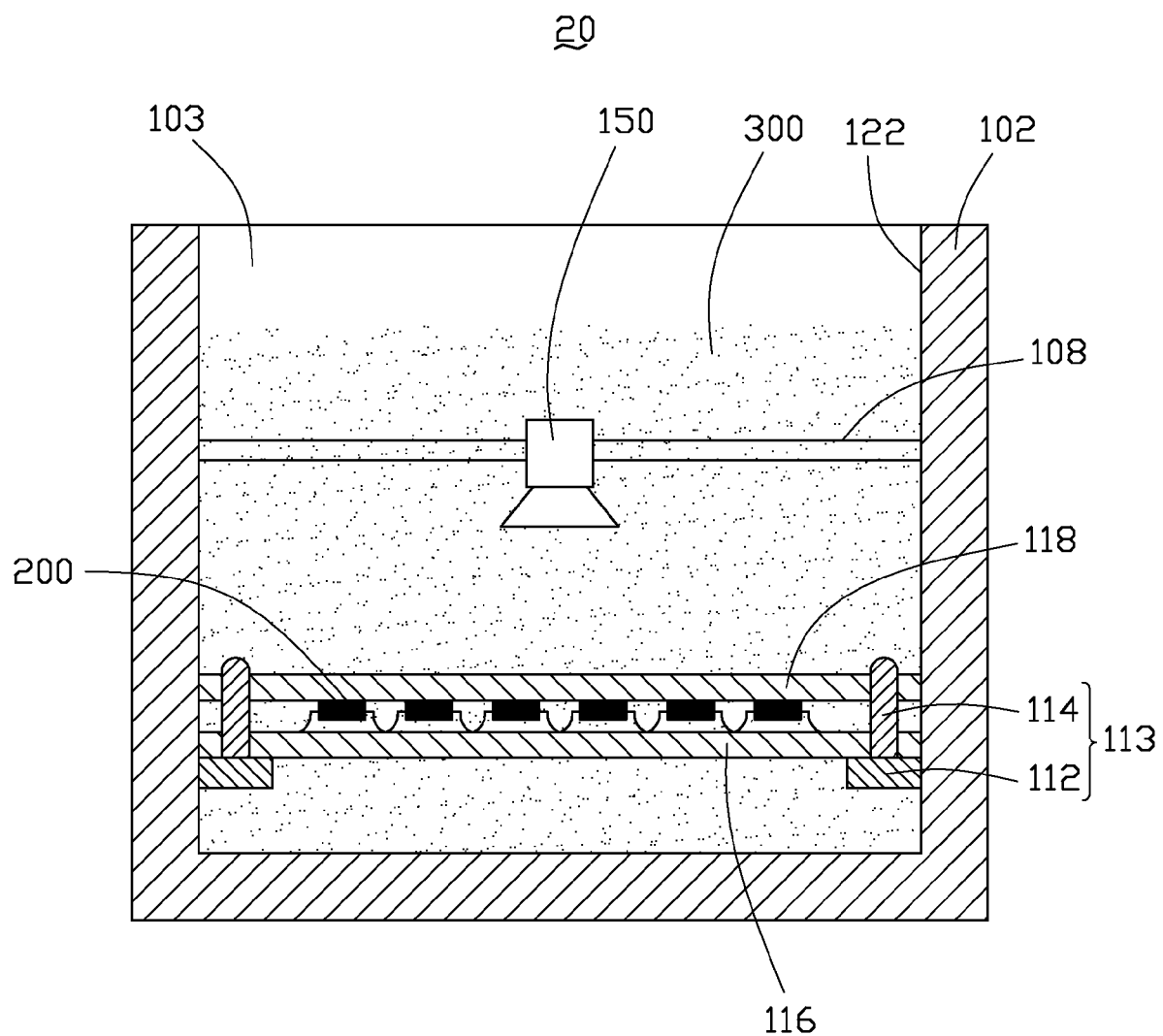
FIG. 4 is a sectional view of a second ultrasonic inspection system in accordance with another exemplary embodiment.

Referring to FIG. 4, a second ultrasonic inspection apparatus 20 in accordance with an alternative embodiment is illustrated. The second ultrasonic inspection apparatus 20 has similar configurations with the first ultrasonic inspection apparatus 10. A main difference between the first ultrasonic inspection apparatus 10 and the second ultrasonic inspection apparatus 20 is that the second ultrasonic inspection apparatus 20 includes a combination member 150 corresponding to the transmitting transducer 104 and the receiving transducer 106 of the first ultrasonic inspection apparatus 20.

Further, the second ultrasonic inspection apparatus 20 only includes one positioning member 108 for attaching the combination member 150 thereto. The combination member 150 not only transmits ultrasonic waves to the ICs 200 to be inspected, but also receives echo ultrasonic waves reflected from the ICs 200. The combination member 150 also provides electrical signals transformed from received echo ultrasonic waves to the computer to detect the defects. Certain detects are identified by measuring the electrical signals, when the ICs 200 is subjected to ultrasonic waves.

As described above, the first ultrasonic inspection apparatus 10 and the second ultrasonic inspection apparatus 20 utilize a loading member 116 and a cover member 118 to firmly hold the ICs 200 to be detected, such that noise due to vibrations or jitters are reduced or eliminated, and the detection precision of the defects is improved accordingly.

The foregoing description of the exemplary embodiments of the invention has been presented only for the purposes of illustration and description and is not intended to be exhaustive or to limit the invention to the precise forms disclosed. Many modifications and variations are possible in light of the above teaching. The embodiments were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

What is claimed is:

1. An ultrasonic inspection apparatus for inspecting integrated circuits for defects, operating by projecting ultrasonic waves from a transmitting transducer and receiving ultrasonic waves passing through or reflected from the integrated circuits by a receiving transducer to detect the defects, the ultrasonic inspection apparatus comprising:

a container containing de-ionized water;

at least one limiting member;

a loading member; and a cover member;

wherein the at least one limiting member, the loading member, and the cover member are disposed in the de-ionized water, and located between the transmitting transducer and the receiving transducer, the limiting member is connected to internal side walls of the container, the loading member is supported on the limiting member for loading the integrated circuits to be detected, the cover member is detachably disposed on the loading member for fixing the integrated circuits between the loading member and the cover member by a gravitational force of the cover member acting on the loading member.

2. The ultrasonic inspection apparatus of claim 1, wherein the at least one limiting member comprises a rib plate connected to internal side walls of the container and a post protruding from the rib plate.

3. The ultrasonic inspection apparatus of claim 1, wherein the cover member and the loading member respectively define through holes, correspondingly, for allowing the post to pass through the through holes successively.

4. The ultrasonic inspection apparatus of claim 1, wherein the cover member has an area larger than that of the loading member.

5. The ultrasonic inspection apparatus of claim 4, wherein the cover member has a width slightly larger than that of the loading member.

6. The ultrasonic inspection apparatus of claim 1, wherein the cover member and the loading member are formed of glass or resin.

7. An ultrasonic inspection apparatus for detecting integrated circuits for defects, the ultrasonic inspection apparatus comprising:

a container defining a cavity for accommodating de-ionized water therein;

a combination member for projecting ultrasonic waves to the integrated circuits and receiving ultrasonic waves reflected from the integrated circuits;

a transmission member coupled to two internal side walls of the container, the transmission member configured to move the combination member in at least two dimensional directions;

at least one limiting member;

a loading member; and a cover member;

wherein the transmission member, the at least one limiting member, the loading member, and the cover member are disposed in the de-ionized water, the limiting member is supported on the limiting member for loading the integrated circuits to be detected, the cover member is detachably disposed on the loading member for holding the integrated circuits by gravitational force of the cover member acting on the loading member.

8. The ultrasonic inspection apparatus of claim 7, wherein the at least one limiting member comprises a rib plate and a post, the rib plate is connected to internal side walls of the container, and the post protrudes from the rib plate.

9. The ultrasonic inspection apparatus of claim 7, wherein the cover member and the loading member define through holes for the post to pass through the through holes successively.

10. The ultrasonic inspection apparatus of claim 7, wherein the cover member has an area larger than that of the loading member.

11. The ultrasonic inspection apparatus of claim 10, wherein the cover member has a width slightly larger than that of the loading member.

12. The ultrasonic inspection apparatus of claim 10, wherein the cover member and the loading member are made of glass or resin.

13. An ultrasonic inspection apparatus for inspecting integrated circuits for defects, the ultrasonic inspection apparatus comprising:
- a container containing de-ionized water;
- a transmitting transducer configured to project ultrasonic waves to the integrated circuits;
- a receiving transducer configured to receive ultrasonic waves passing through the integrated circuits from one side to another side to detect the defects;
- at least one limiting member disposed in the de-ionized water, and connected to internal side walls of the container;
- a loading member supported on the limiting member for loading the integrated circuits to be detected; and
- a cover member disposed in the de-ionized water, and located between the transmitting transducer and the receiving transducer, the cover member detachably disposed on the loading member for holding the integrated circuits between the loading member and the cover member by a gravitational force of the cover member acting on the loading member.

14. The ultrasonic inspection apparatus of claim 13, further comprising a first positing member and a second positioning member that are disposed in the de-ionized water, the first positioning member and the second positioning member configured to respectively move the transmitting transducer and the receiving transducer in synchronization in at least two dimensional directions.

* * * * *